(12) United States Patent
Cronenberg et al.

(10) Patent No.: US 10,765,813 B2
(45) Date of Patent: *Sep. 8, 2020

(54) SELF INJECTION DEVICE WITH MULTI-POSITION CAP

(71) Applicant: Becton, Dickinson and Company, Franklin Lakes, NJ (US)

(72) Inventors: Richard Cronenberg, Mahwah, NJ (US); Ruane Jeter, Hattiesburg, MS (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 102 days.

This patent is subject to a terminal disclaimer.

(21) Appl. No.: 15/602,785

(22) Filed: May 23, 2017

(65) Prior Publication Data

US 2017/0252519 A1 Sep. 7, 2017

Related U.S. Application Data

(63) Continuation of application No. 13/513,073, filed as application No. PCT/US2010/003085 on Dec. 3, 2010, now Pat. No. 9,675,762.

(60) Provisional application No. 61/266,697, filed on Dec. 4, 2009.

(51) Int. Cl.
| A61M 5/32 | (2006.01) |
| A61M 5/31 | (2006.01) |
| A61M 5/24 | (2006.01) |
| A61M 5/315 | (2006.01) |

(52) U.S. Cl.
CPC ........ *A61M 5/3202* (2013.01); *A61M 5/3134* (2013.01); *A61M 5/3213* (2013.01); *A61M 5/24* (2013.01); *A61M 5/31525* (2013.01); *A61M 5/31533* (2013.01); *A61M 2005/2407* (2013.01); *A61M 2005/3104* (2013.01)

(58) Field of Classification Search
CPC .............. A61M 5/3202; A61M 5/3213; A61M 2005/3104
See application file for complete search history.

(56) References Cited

U.S. PATENT DOCUMENTS

| 2,828,742 | A |   | 4/1958  | Ashkenaz |
| 3,107,785 | A | * | 10/1963 | Roehr .................. A61M 5/002 |
|           |   |   |         | 206/365 |
| 5,112,315 | A |   | 5/1992  | Gloyer et al. |
| 5,248,299 | A |   | 9/1993  | Ota |
| 5,250,037 | A |   | 10/1993 | Bitdinger |
| 5,595,566 | A |   | 1/1997  | Vallelunga et al. |

(Continued)

FOREIGN PATENT DOCUMENTS

| CN | 1466471   | 1/2004 |
| EP | 0820779 B1 | 1/1998 |

(Continued)

*Primary Examiner* — Bradley J Osinski
(74) *Attorney, Agent, or Firm* — Dickinson Wright PLLC

(57) ABSTRACT

A self-injection device (100, 200), including a pen body (108, 208) connectable to a pen needle (10), and a cap (104, 204) selectively connectable to the pen body (108, 208) in a first orientation with respect to the pen body (108, 208) to minimize the length or volume of the self injection device (100, 200), and in a second orientation to provide sufficient length or volume in an interior of the cap (104, 204) to house a pen needle (10) connected to the pen body (108, 208).

21 Claims, 11 Drawing Sheets

(56) References Cited

U.S. PATENT DOCUMENTS

| | | |
|---|---|---|
| 5,843,047 A | 12/1998 | Pyrozyk et al. |
| 6,454,746 B1 | 9/2002 | Bydlon et al. |
| 6,752,798 B2 | 6/2004 | Mcwethy et al. |
| 6,767,336 B1 | 7/2004 | Kaplan |
| 7,001,364 B1 | 2/2006 | Farhi |
| 7,066,909 B1 | 6/2006 | Peter et al. |
| 7,449,012 B2 | 11/2008 | Young et al. |
| 7,666,164 B2 | 2/2010 | Giambattista |

FOREIGN PATENT DOCUMENTS

| | | |
|---|---|---|
| EP | 0744975 B1 | 9/2001 |
| FR | 2992222 | 12/2013 |
| JP | 2001-516235 | 9/2001 |
| JP | 2002-502296 | 1/2002 |
| JP | 4290798 B2 | 4/2009 |
| WO | WO-9205820 | 4/1992 |
| WO | WO-0209797 | 2/2002 |

\* cited by examiner

SELF INJECTION DEVICE WITH MULTI-POSITION CAP

CROSS-REFERENCE TO RELATED APPLICATION

This application is a continuation of U.S. patent application Ser. No. 13/513,073, filed on Jul. 20, 2012, which is the U.S. national stage of International Application No. PCT/US10/03085, filed on Dec. 3, 2010, which claims the benefit of U.S. Provisional Patent Application Ser. No. 61/266,697, filed Dec. 4, 2009 at the U.S. Patent and Trademark Office, the disclosures of which are incorporated herein by reference in their entirety.

FIELD OF THE INVENTION

The present invention relates generally to a self-injection device, and more particularly to self-injection device with a multi-position cap.

BACKGROUND OF THE INVENTION

Medication delivery pens are hypodermic syringes used for self-injection of precisely measured doses of medication. Pens are widely used, for example, by diabetics to self-inject insulin. A typical prior art medication delivery pen includes a cartridge which contains a volume of liquid medication sufficient for several doses. The dose is injected into a tissue area, such as the intramuscular tissue layer, the subcutaneous tissue layer, or the intradermal tissue layer.

The assembly and operation of a typical pen injection device is described in commonly-assigned U.S. Pat. No. 7,645,264, issued on Jan. 12, 2010, which is incorporated herein by reference in its entirety.

Pen injection devices, such as the exemplary pen injector 50, as shown in FIGS. 1 and 2, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is employed by the user to securely hold the pen injector 50 in a shirt pocket, purse, or other suitable location.

FIG. 2 is an exploded view of the exemplary drug delivery pen 50 shown in FIG. 1. The dose knob/button 24 has a dual purpose and is used to both set the dosage of the medication to be injected and to inject the dosed medicament via a lead screw 7 and stopper 15 from a medicament cartridge 12, which is attached to the drug delivery pen through a lower housing 17. The lower housing 17 typically has dosage indicia on the exterior thereof. The medicament cartridge 12 is typically a glass tube sealed at one end with a septum 16 and at the other end with the stopper 15. In standard drug delivery pens, the dosing and delivery mechanisms are all found within the outer sleeve 13. Those mechanisms are not described in greater detail here as they are understood by those knowledgeable of the art.

A pen needle assembly 10 (hereinafter referred to as pen needle 10 for brevity) includes a hub 20, a patient needle 11 extending from a patient end of the pen needle, and a septum-penetrating needle cannula 18 disposed within the hub 20 on a non-patient side thereof. The septum-penetrating needle cannula 18 is in fluid communication with the patient needle 11. The hub 20 is preferably screwed onto the lower housing 17. In attaching the hub 20 to the lower housing 17, the septum-penetrating cannula 18 pierces the septum 16, but the septum 16 does not move with respect to the medicament cartridge 12. The stopper 15, however, is axially displaceable within the medicament cartridge 12 while maintaining a fluid tight seal. The distal movement of the plunger or stopper 15 within the medicament cartridge 12 (due to advancement of the lead screw 7) causes medication to be forced into the patient needle 11 of the hub 20.

To protect a user, or anyone who handles the pen needle assembly 10, an outer shield 29, which attaches to the hub 20, covers the hub 20. The outer shield 29 can also be used as a handle or grip to screw hub 20 onto or off pen injector 50. An inner shield 28 covers the patient needle 11 within the outer shield 29. The inner shield 28 can be secured to the hub 20 to cover the patient needle 11 by any suitable means, such as an interference fit or a snap fit. The outer shield 29 and inner shield 28 are removed prior to use. The cap 21 fits snugly against outer sleeve 13 to allow a user to securely carry the pen injection device 50.

A pen injector, such as pen injector 50, can be designed to have the shortest length possible, or it can be designed to protect a pen needle 10 that has already been assembled to the pen injector 50. While it is highly desirable to produce the shortest, smallest pen possible, there are times when a user might want to pre-assemble a pen needle 10 to a pen injector. For example, a user may be going to a restaurant to eat and may need to provide an injection of very fast acting insulin just prior to eating. When timed properly, such an injection provides a more consistent glucose level. But the injection cannot be given too far in advance because the user's glucose level will drop too much. This situation effectively requires that the injection be given at the restaurant. For convenience, the user may wish to pre-assemble the pen needle 10 with the pen injector so that it is ready to use. If the pen injector 50 is designed to protect an assembled pen needle 10 within the cap 21 when the pen needle 10 is not assembled with the pen injector 50, the pen injector 50 is longer than it needs to be, and thus takes up more space. What is needed is a pen injector that can accomplish both modalities, one in which the pen injector is as small as possible, and one in which a pen needle can be accommodated while assembled to the pen injector.

SUMMARY OF THE INVENTION

An aspect of the present invention is to provide a self-injection device with a body and a cap that can accommodate and protect a pen needle assembled to the body in a first mode, and that can minimize the size of the self-injection device in a second mode.

The foregoing and/or other aspects of the present invention are achieved by providing a self-injection device, including a pen body connectable with a pen needle, and a cap selectively connectable to the pen body in a first orientation with respect to the pen body to minimize the length or volume of the self injection device, and in a second orientation to provide sufficient length or volume in an interior of the cap to house a pen needle connected with the pen body.

The foregoing and/or other aspects of the present invention are also achieved by providing a self-injection device, including a body selectively connectable with a pen needle at a first end of the body, and a cap having an interior cavity, the cap being connectable to the body in a first orientation with respect to the body, and in a second orientation with respect to the body that is axially further from a second end of the body than the first orientation, to accommodate the pen needle connected to the body within the interior cavity, the second end of the body being opposite to the first end.

The foregoing and/or other aspects of the present invention are also achieved by providing a method using a self-injection device comprising a body and a cap, the method including the operations of: at a first time, connecting the cap with the body in a first orientation in which the length or volume of the of the self-injection device is minimized; and at a second time, connecting the cap with the body in a second orientation in which, with respect to the first orientation, a length or volume in an interior of the cap is increased to house a pen needle connected with the pen body.

Additional and/or other aspects and advantages of the present invention will be set forth in part in the description that follows and, in part, will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, in which.

DETAILED DESCRIPTION OF EXEMPLARY EMBODIMENTS

Figure 1:
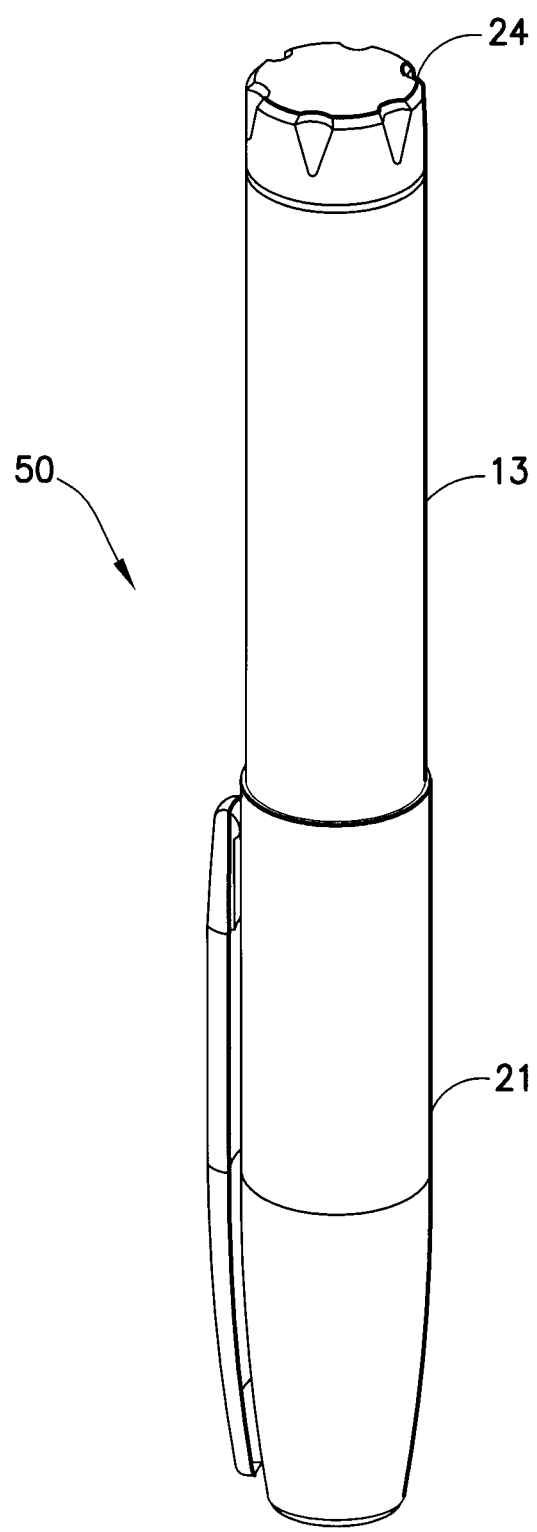
FIG. 1 is a perspective view of an exemplary drug delivery pen.
Figure 2:
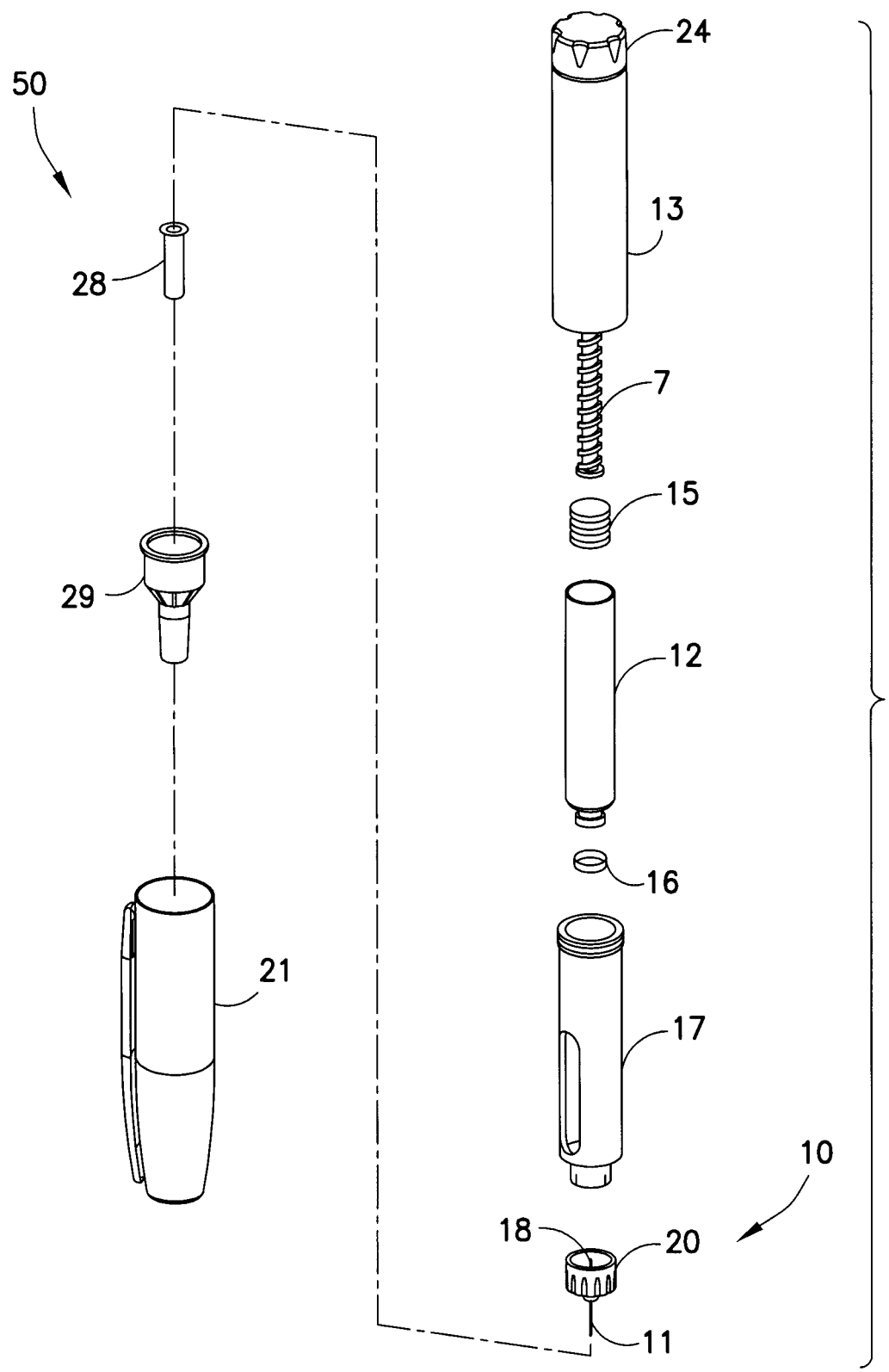
FIG. 2 is an exploded view of the exemplary drug delivery pen of FIG. 1.

Reference will now be made in detail to embodiments of the present invention, examples of which are illustrated in the accompanying drawings, wherein like reference numerals refer to the like elements throughout. The descriptions of these embodiments exemplify the present invention by referring to the drawings.

Figure 3:
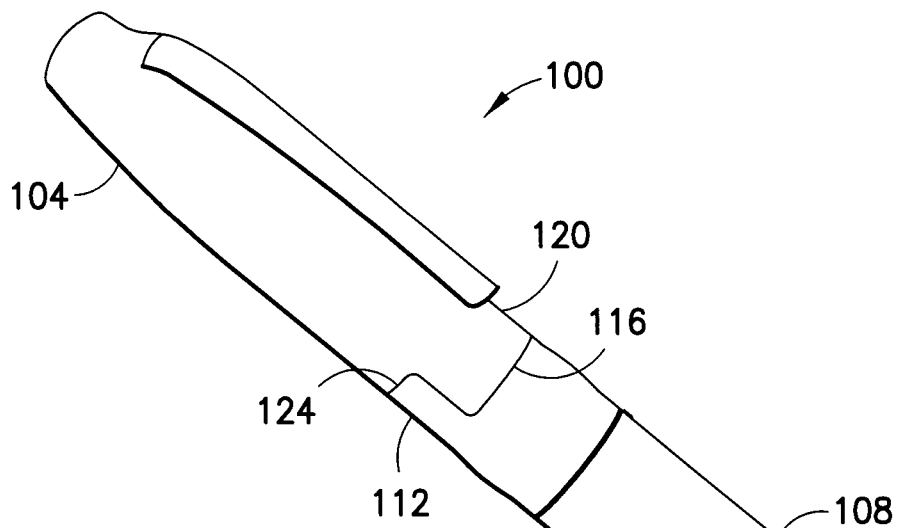
FIG. 3 is a perspective view of a self-injection device in a first orientation in accordance with an embodiment of the present invention.
Figure 4:
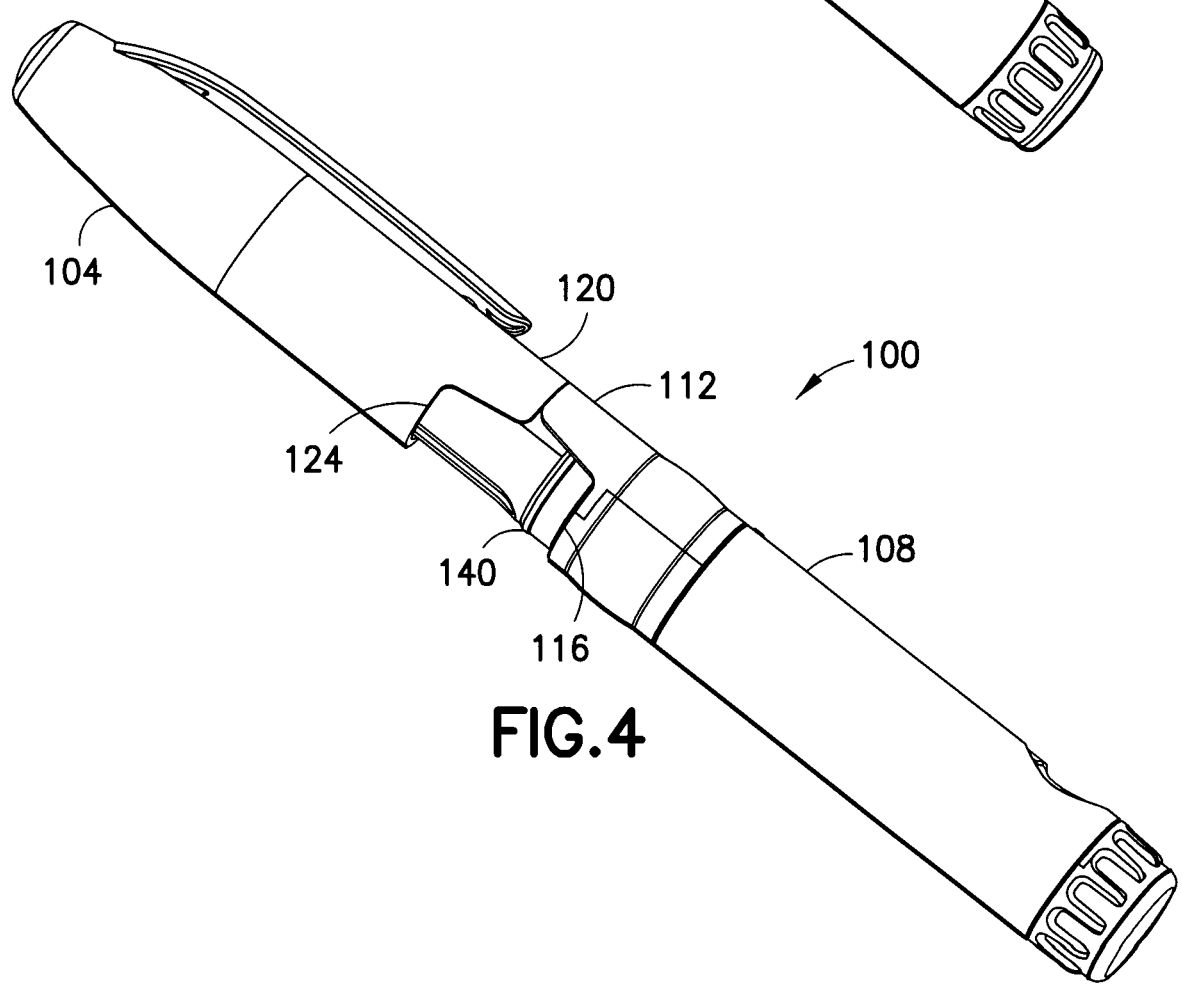
FIG. 4 is a perspective view of a the self-injection device of FIG. 3 in a second orientation.

FIGS. 3 and 4 are perspective views illustrating first and second connection orientations of a self-injection device 100 in accordance with an embodiment of the present invention. As shown in FIGS. 3 and 4, the self-injection device (or pen injector) 100 includes a cap 104 and a body or pen body 108. The cap 104 and the body 108 are connectable to each other in first (for example, FIG. 3) and second (for example, FIG. 4) radial orientations. In FIG. 3, the cap 104 is connected with the body 108 in the first orientation to be as compact as possible. In other words, the overall volume and/or length of the pen injector 100 are minimized in the first orientation. In FIG. 4, the cap 104 is radially rotated with respect to the first orientation, and is connected to the body 108 in the second orientation to allow a pen needle 10 to be protected inside the cap 104. In other words, in the second radial orientation, there is sufficient volume and/or length in an interior of the cap 104 to house the pen needle 10 connected with the body 108.

The body 108 includes an axial protrusion 112 and an axial recess 116. Similarly, the cap 104 includes an axial protrusion 120 and an axial recess 124. In the first orientation, the respective axial protrusions 112 and 120 abut the respective axial recesses 116 and 124. In other words, as shown in FIG. 3, the body axial protrusion 112 abuts the cap axial recess 124 and the cap axial protrusion 120 abuts the body axial recess 116. In the second orientation, as shown in FIG. 4, body axial protrusion 112 abuts cap axial protrusion 120. In the first and second orientations, the cap 104 encloses the distal end of the body 108, as shown, for example, in FIGS. 3-6.

Figure 5:
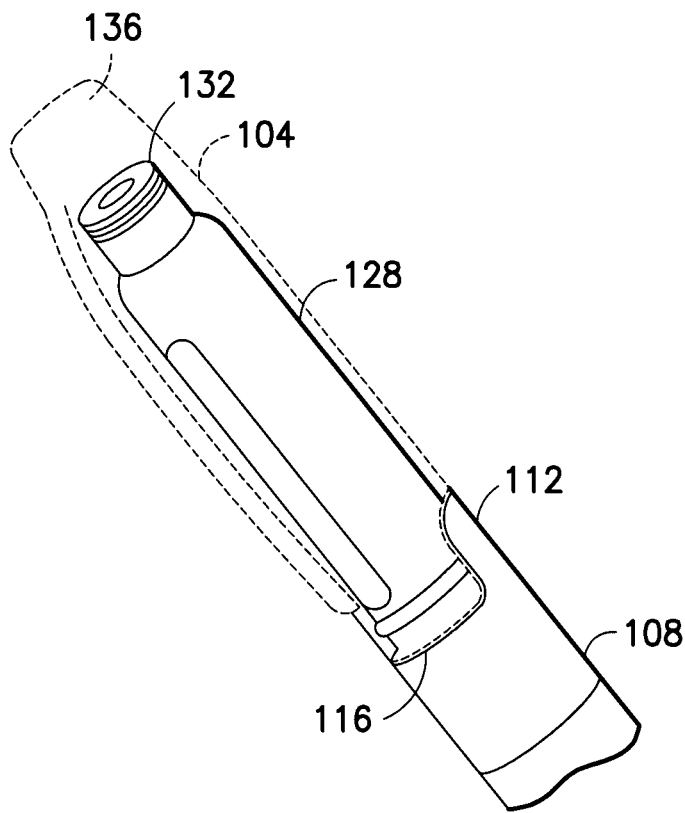
FIGS. 5 and 6 are partial perspective views respectively illustrating the first and second orientations of the self-injection device of FIG. 3.
Figure 6:
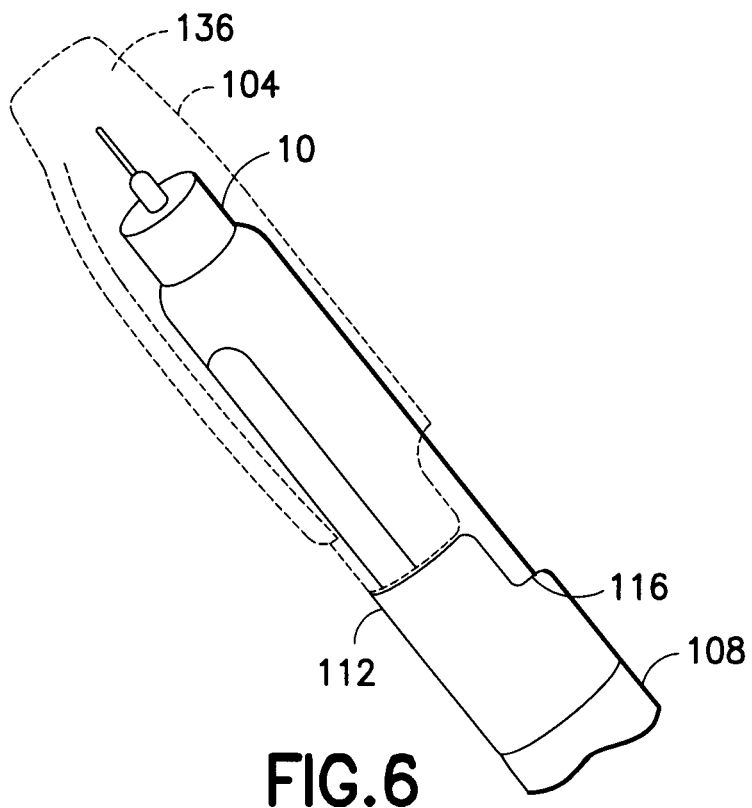

FIGS. 5 and 6 respectively illustrate further details of the first and second orientations. In FIGS. 5 and 6, the cap 104 is shown in dotted lines for clarity. As shown in FIG. 5, an outer sleeve or cartridge container 128 of the body 108 includes a screw thread 132 at a first end of the body 108 for connecting a pen needle 10 thereto. The cartridge container 128 holds a medicament cartridge in the body 108. In the first orientation, there is insufficient space in an interior cavity 136 of the cap 104 to accommodate a pen needle 10. In contrast, as shown in FIG. 6, in the second orientation, cap 104 protectively houses the pen needle 10.

Figure 7:
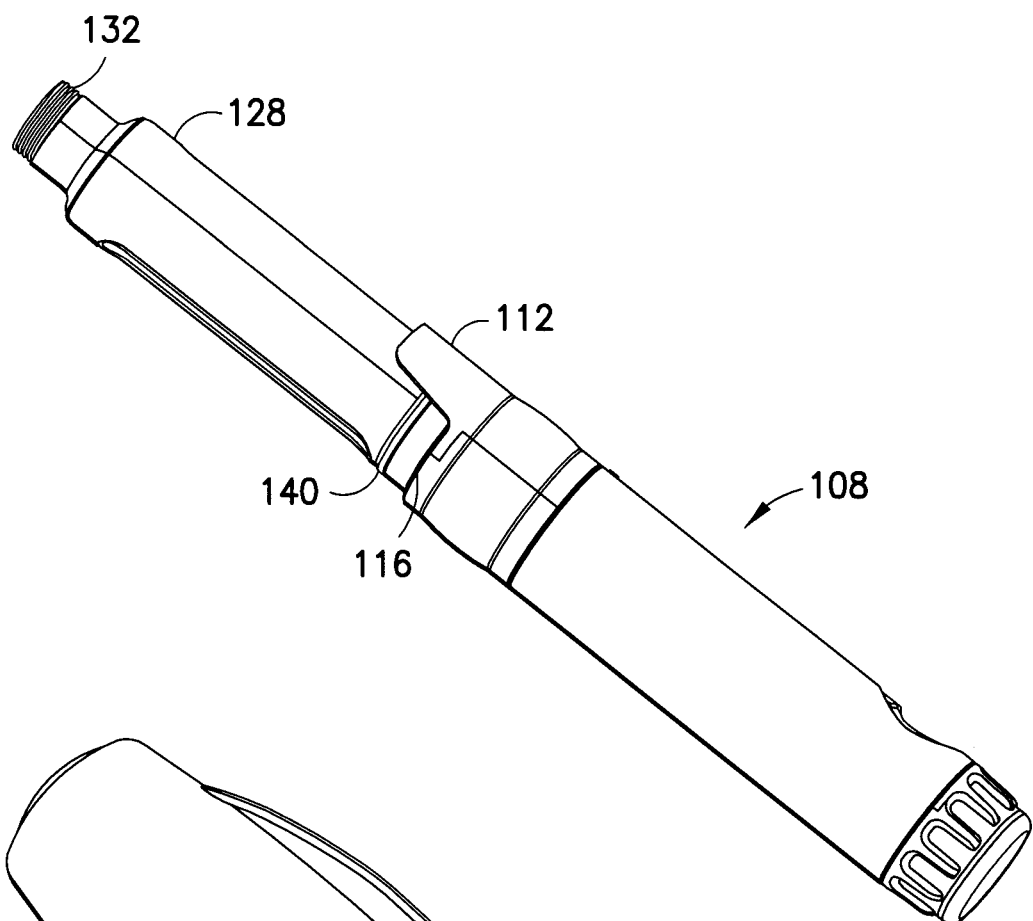
FIG. 7 is a perspective view of a body of the self-injection device of FIG. 3.
Figure 8:
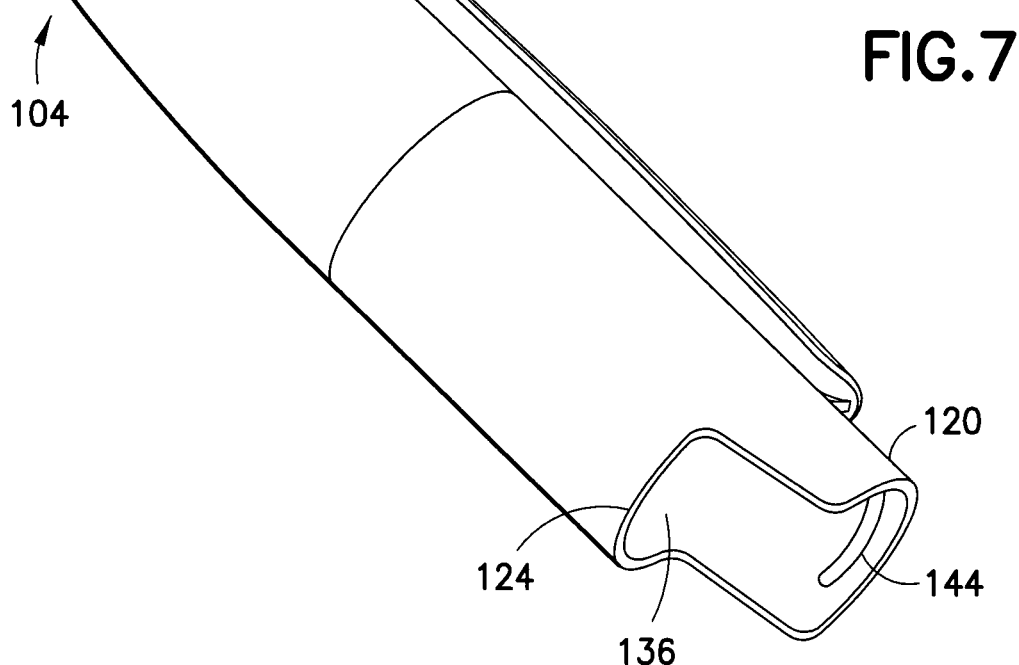
FIG. 8 is a perspective view of the cap of the self-injection device of FIG. 3.

FIG. 7 is a perspective view of the body 108 and FIG. 8 is a perspective view of the cap 104. As shown in FIG. 7, the body 108 includes a first body connector 140 disposed within the body axial recess 116. Correspondingly, as shown in FIG. 8, the cap 104 has a cap connector 144 disposed on an interior of the cap axial protrusion 120. As shown, the first body connector 140 is embodied as a radial protrusion and the cap connector 144 is embodied as a radial recess, but one skilled in the art will appreciate that the body connector 140 may be embodied as a radial recess and the cap connector 144 may be embodied as a radial protrusion without departing from the scope of the present invention. In addition, one skilled in the art will appreciate that the first body connector 140 and the cap connector 144 may be embodied as other types of connectors without departing from the scope of the present invention.

Figure 9:
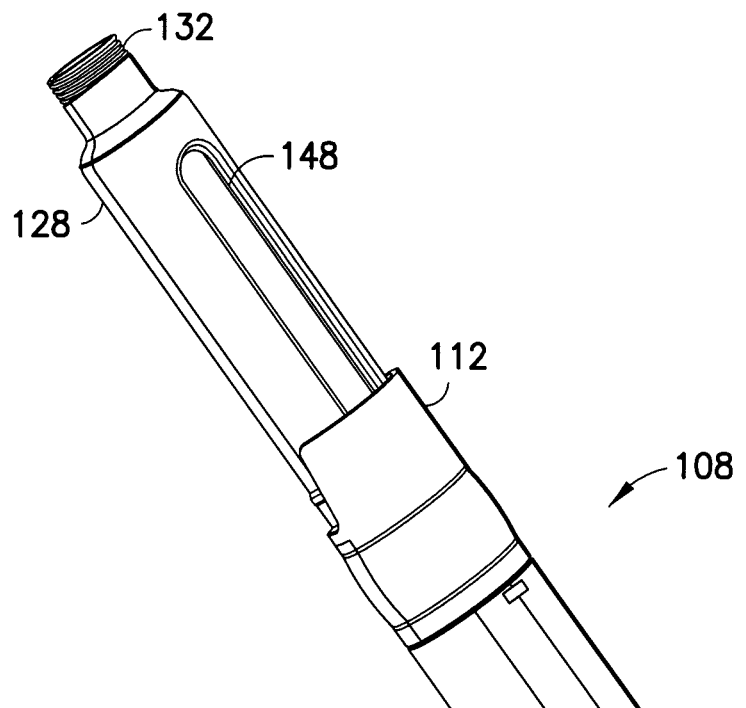
FIG. 9 is another perspective view of a body of the self-injection device of FIG. 3.
Figure 10:
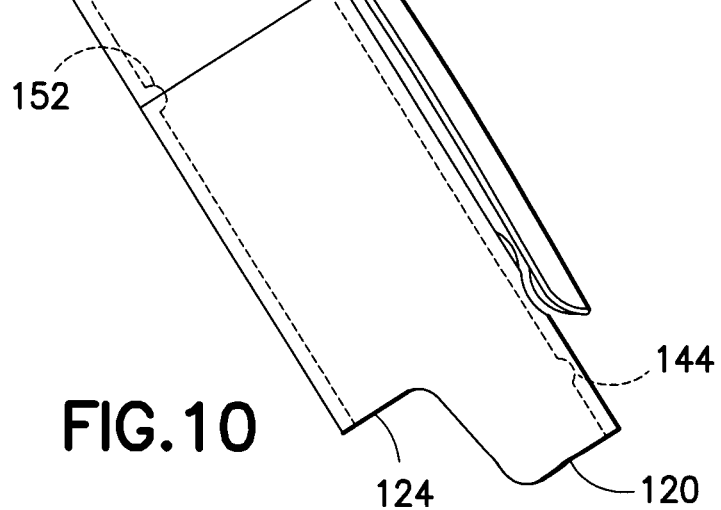
FIG. 10 is a perspective view illustrating a connection mechanism of the self-injection device of FIG. 3

Showing another perspective view of the body 108, FIG. 9 illustrates an axial slot 148 of the cartridge container 128. Through the axial slot 148, the user can view the progress of the stopper (such as stopper 15) in the medicament cartridge (such as cartridge 12). FIG. 10 is a perspective view of the cap 104 in which an interior surface of the cap 104 is shown in dotted lines. A radial connecting protrusion 152 projects inwardly from the interior surface of the cap 104. According to one embodiment, to secure the cap 104 and the body 108 in the second orientation, the radial connecting protrusion 152 engages the axial slot 148.

Figure 11:
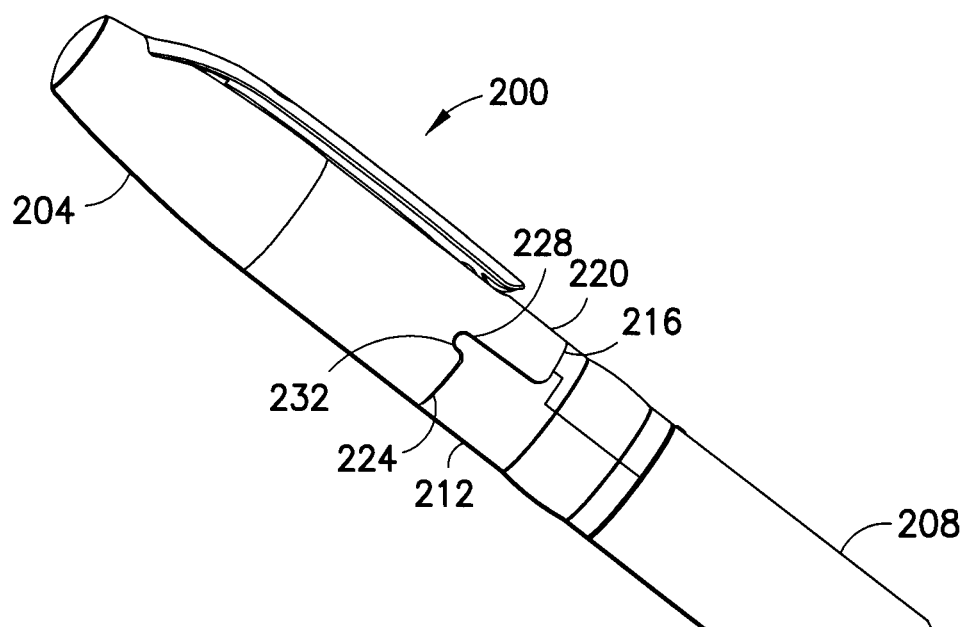
FIG. 11 is a perspective view of a self-injection device in accordance with another embodiment of the present invention.

FIG. 11 is a perspective view of another pen injector 200 in accordance with an embodiment of the present invention. Like the embodiment of FIGS. 3-10, the pen injector 200 has a cap 204 and a body 208 with respective axial protrusions 212 and 220 and axial recesses 216 and 224. In addition, the pen injector 200 has an anti-rotation feature for preventing radial rotation of the cap 204 relative to the body 208, and therefore, preventing inadvertent collapse of the cap 204 onto a pen needle 10 assembled to the body 208.

Figure 15:
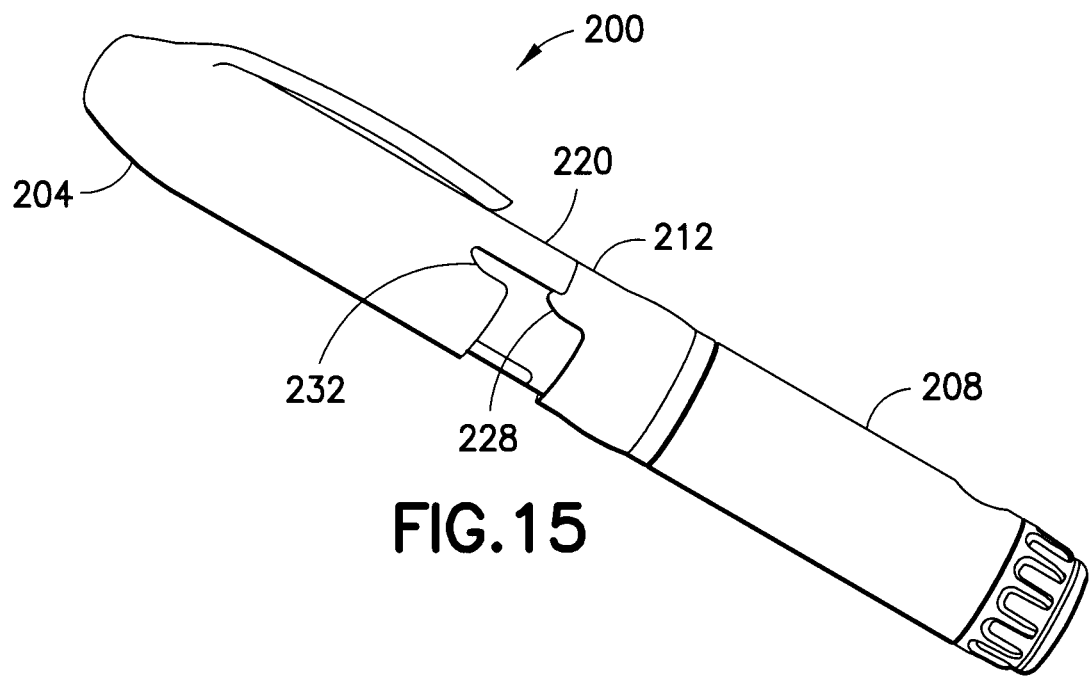
FIG. 15 is a perspective view of the self-injection device of FIG. 11 in the second orientation.

According to one embodiment, the anti-rotation feature includes an axial horn protrusion 228 disposed on a top, radial side of the body axial protrusion 212, and a corresponding axial horn recess 232 disposed on a radial side of the cap axial recess 224. As shown in FIGS. 11-14, according to one embodiment, the anti-rotation feature includes a pair of axial horn protrusions (or horns) 228 and a pair of corresponding axial horn recesses 232. When the cap 204 is secured with the body 208 in the first orientation, as shown in FIG. 11, the horns 228 interact with the horn recesses 232 to prevent rotation of the cap 204 relative to the body 208. In contrast, when the cap 204 is secured with the body 208 in the second orientation, as shown in FIG. 15, the horns 228 interact with radial sides of the cap axial protrusion 220 to prevent rotation of the cap 204 relative to the body 208.

Figure 16:
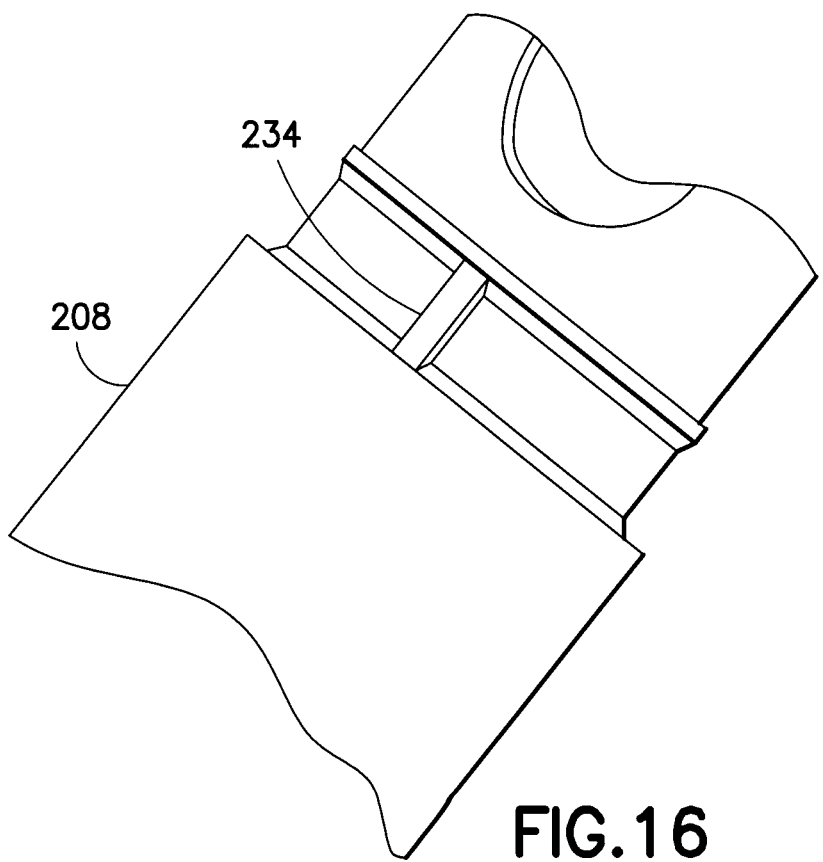
FIGS. 16 and 17 are perspective views illustrating an anti-rotation feature in accordance with an embodiment of the present invention.
Figure 17:
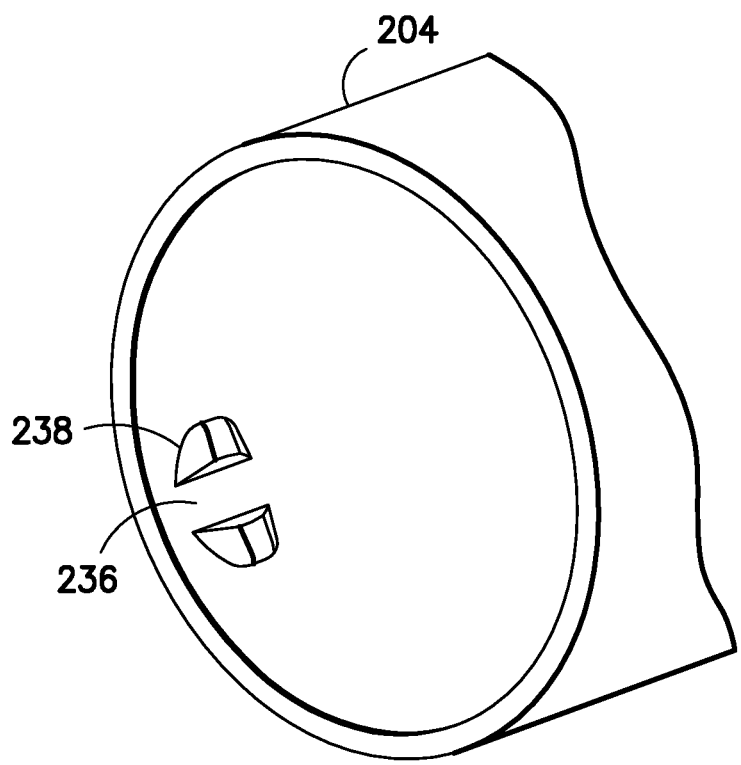
Figure 18:
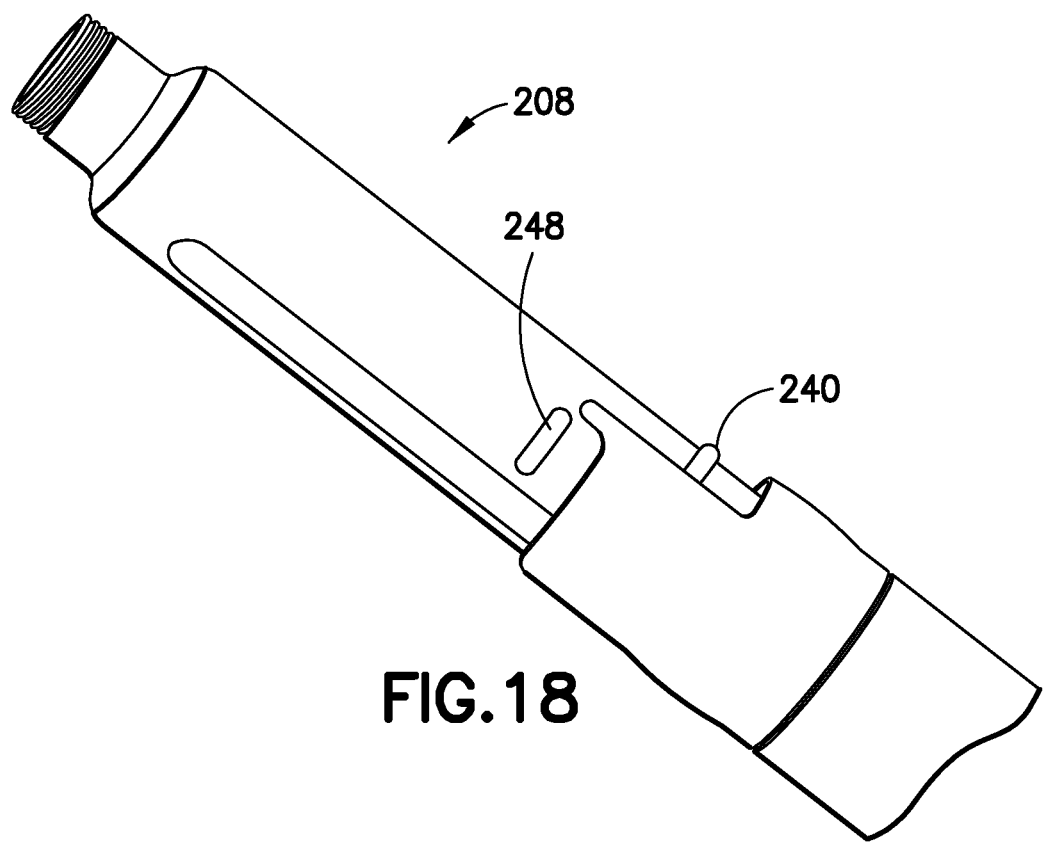
FIG. 18 is a perspective view of the body of the self-injection device of FIG. 11 illustrating a connection mechanism thereof.

According to another embodiment, as shown in FIGS. 16 and 17, the anti-rotation feature includes a key 234 axially disposed on the body 208 and a corresponding slot 236 formed between a pair of radial slot protrusions 238 disposed on the interior of the cap 204. When the key 234 is disposed in the slot 236, the cap 204 is prevented from radially rotating with respect to the body 208. Although the key 234 and slot 236 are illustrated as preventing rotation in the first orientation, the key 234 and slot 236 may be positioned axially further away from a second end of the body 208 opposite to the first end, and thereby prevent rotation in the second orientation. Alternatively, keys 234 and slots 236 may be disposed at both locations to prevent relative rotation in both the first and the second orientations.

Although the horns 228 are illustrated as being disposed on the body 208 and the horn recesses 232 are illustrated as being disposed on the cap 204, one skilled in the art will appreciate that the horns 228 may be disposed on the cap 204 and the corresponding horn recesses 232 may be disposed on the body 208 without departing from the scope of the present invention. Similarly, although the key 234 is illustrated as being disposed on the body 208 and the slot 236 is illustrated as being disposed on the cap 204, one skilled in the art will appreciate that the key 234 may be disposed on the cap 204 and the corresponding slot 236 may be disposed on the body 208 without departing from the scope of the present invention.

Additionally, although the embodiment shown in FIGS. 11-15 illustrates horns 228 and horn recesses 232, and FIGS. 16 and 17 illustrate a slot 236 and a key 234, one skilled in the art will appreciate that, without departing from the scope of the present invention, other shapes may be used to prevent inadvertent rotation of the cap 204 relative to the body 208 and thereby prevent the cap 204 from moving out of the second orientation and moving axially toward the second end of the body 208.

Figure 12:
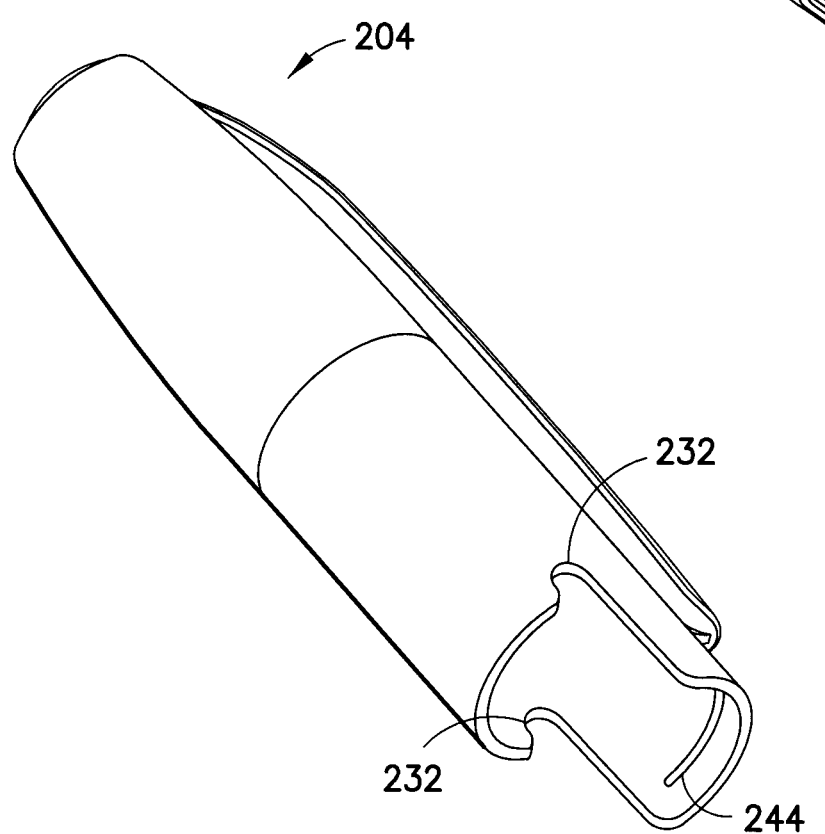
FIG. 12 is a perspective view of a cap of the self-injection device of FIG. 11.
Figure 13:
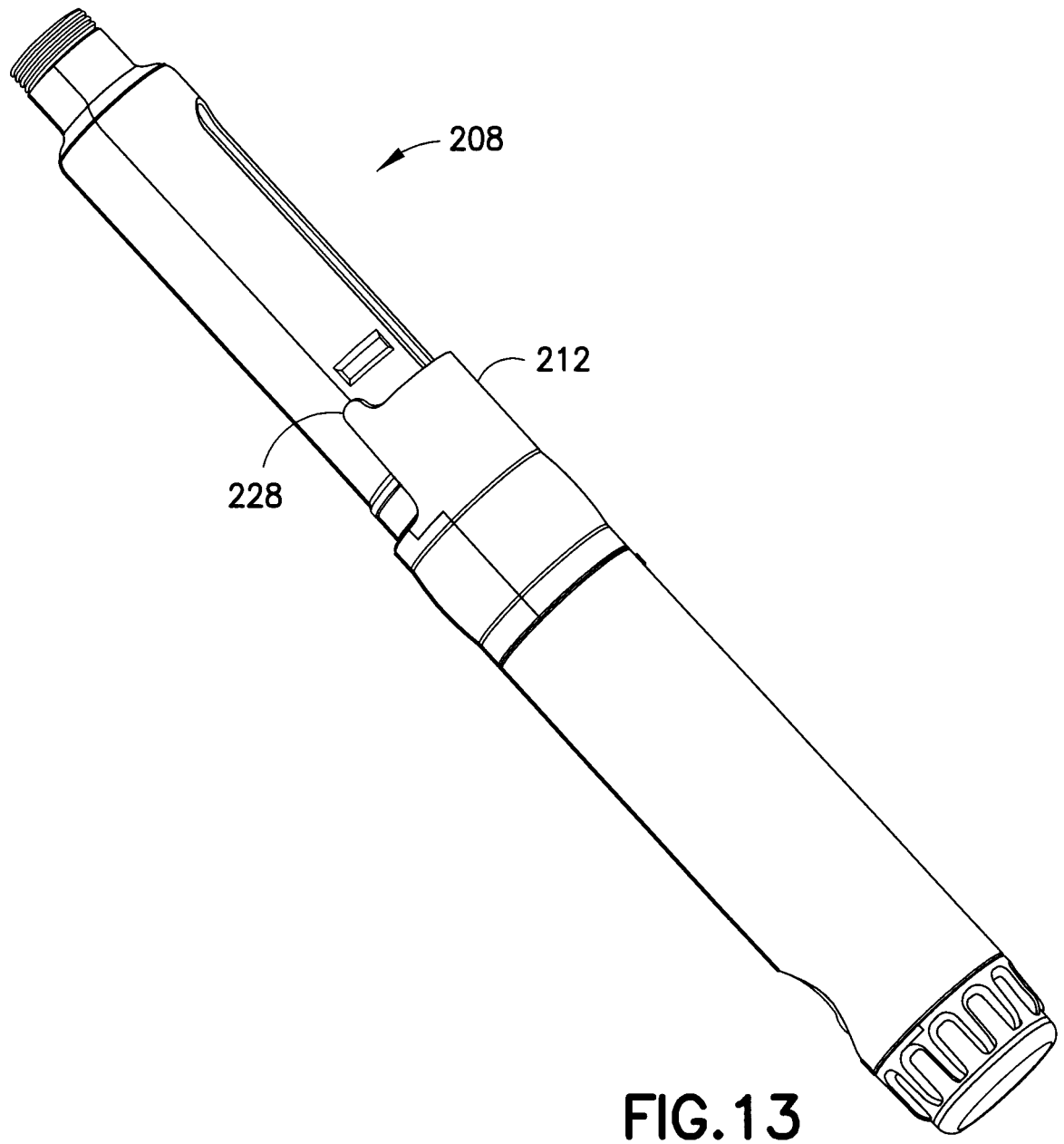
FIG. 13 is a perspective view of a body of the self-injection device of FIG. 11.
Figure 14:
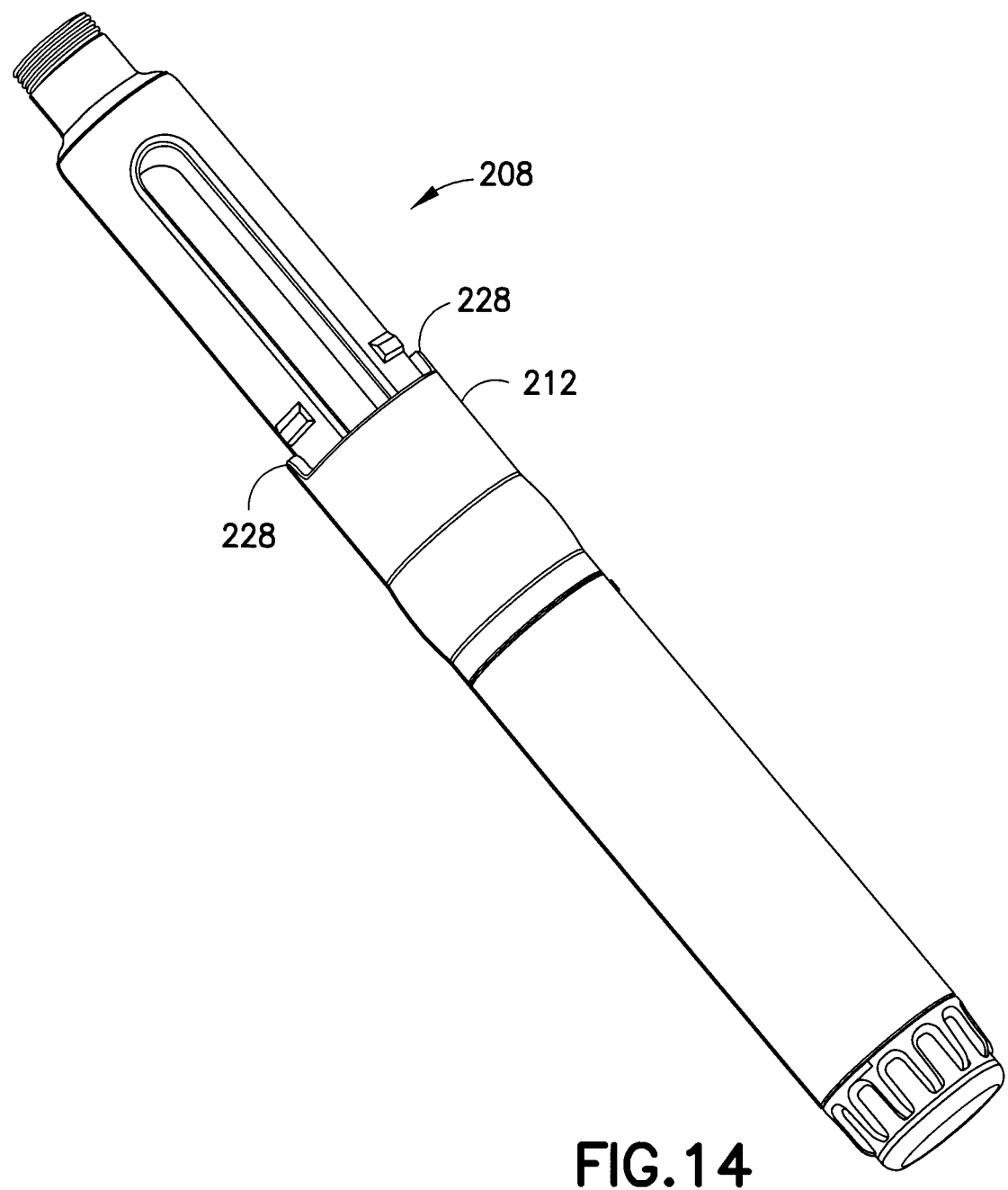
FIG. 14 is another perspective view of the body of the self-injection device of FIG. 11.

To secure the cap 204 to the body 208 in the first orientation, similar to the embodiment of FIGS. 3-10, the body 208 includes a first body connector 240 and the cap 204 includes a cap connector 244 (see FIG. 12). According to one embodiment, the first body connector is a radial protrusion and the cap connector 244 is a corresponding radial recess. One skilled in the art will appreciate that the cap connector may be a radial protrusion and the first body connector 240 may be a corresponding radial recess without departing from the scope of the present invention. As shown in FIG. 16, however, to secure the cap 204 to the body 208 in the second orientation, the body includes a second body connector 248. In the second orientation, the radially protruding second body connector interacts with the correspondingly radially recessed cap connector 244 to provide a snap-fit connection to secure the cap 204 to the body 208.

Although the radial connecting protrusion 152 is illustrated as the connection mechanism for securing the cap to the body in the second orientation in the embodiment shown in the first embodiment shown in FIGS. 3-10, and the second body connector 248 is illustrated as the connection mechanism for securing the cap to the body in the second orientation in the second embodiment shown in FIGS. 11-16, one skilled in the art will appreciate that the connecting protrusion 152 may be employed with the second embodiment and the second body connector 248 may be employed with first embodiment, without departing from the scope of the present invention.

Embodiments of the present invention provide a cap that is connectable to the body in a first orientation in which the cap is as compact as possible to allow the smallest pen injector. Additionally, the cap is connectable to the body in another orientation to provide space for protection for a pen needle that has been assembled to the pen injector.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of the appended claims and equivalents thereof.

The invention claimed is:

1. A self-injection device, comprising:
   a pen needle;
   a pen body connectable to the pen needle; and
   a cap connectable directly to a first end of the pen body:
      in a first orientation with respect to the pen body to render a length or volume of the self-injection device insufficient to house the pen needle connected to the pen body; and
      in a second orientation to provide sufficient length or volume in an interior of the cap to house the pen needle connected to the pen body.

2. The self-injection device according to claim 1, wherein the first and second orientations are radial orientations with respect to the pen body.

3. A self-injection device, comprising:
   a pen needle;
   a pen body connectable to the pen needle; and
   a cap connectable to the pen body in a first orientation with respect to the pen body to render a length or volume of the self-injection device insufficient to house the pen needle connected to the pen body, and in a second orientation to provide sufficient length or volume in an interior of the cap to house the pen needle connected to the pen body;

wherein:
the pen body comprises a pen body axial protrusion and a pen body axial recess, and the cap comprises a cap axial protrusion and a cap axial recess;
in the first orientation, the pen body axial protrusion axially abuts the cap axial recess and the cap axial protrusion axially abuts the pen body axial recess; and
in the second orientation, the pen body axial protrusion axially abuts the cap axial protrusion.

4. The self-injection device according to claim 3, wherein:
the pen body comprises a first body connector disposed within the pen body axial recess;
the cap comprises a cap connector disposed on an interior of the cap axial protrusion axially adjacent to an end of the cap axial protrusion to interact with the first body connector to secure the cap to the pen body in the first orientation; and
the first body connector comprises one of a radial protrusion and a radial recess, and the cap connector comprises a remaining one of the radial protrusion and the radial recess.

5. The self-injection device according to claim 4, wherein:
the pen body further comprises a second body connector disposed axially adjacent to an end of the pen body axial protrusion; and
the second body connector comprises one of a second radial protrusion and a second radial recess, to interact with the cap connector to secure the cap to the pen body in the second orientation.

6. The self-injection device according to claim 4, wherein:
the pen body further comprises a cartridge container for holding a medicament cartridge in the pen body, the cartridge container having an axial slot therethrough for viewing content of the medicament cartridge; and
the cap further comprises a radial protrusion that engages the cartridge container axial slot to secure the cap to the pen body in the second orientation.

7. The self-injection device according to claim 3, further comprising an anti-rotation feature for preventing rotation of the cap with respect to the pen body subsequent to connection of the cap to the pen body.

8. The self-injection device according to claim 7, wherein the anti-rotation feature comprises:
a pair of axially protruding horns disposed on radial sides of the pen body axial protrusion; and
a pair of axial horn recesses disposed on radial sides of the cap axial recess, the horn recesses corresponding to the horns;
wherein the horns interact with horn recesses when the cap is secured to the pen body in the first orientation to prevent relative rotation of the cap with respect to the pen body; and
wherein the horns interact with radial sides of the cap axial protrusion when the cap is secured to the pen body in the second orientation to prevent relative rotation of the cap with respect to the pen body.

9. The self-injection device according to claim 7, wherein the anti-rotation feature comprises:
a pair of axially protruding horns disposed on radial sides of the cap axial protrusion; and
a pair of axial horn recesses disposed on radial sides of the pen body axial recess, the horn recesses corresponding to the horns;
wherein the horns interact with horn recesses when the cap is secured to the pen body in the first orientation to prevent relative rotation of the cap with respect to the pen body; and
wherein the horns interact with radial sides of the pen body axial protrusion when the cap is secured to the pen body in the second orientation to prevent relative rotation of the cap with respect to the pen body.

10. A self-injection device, comprising:
a pen needle;
a body connectable to the pen needle at a first end of the body;
a cap having an interior cavity, the cap being connectable directly to the first end of the body:
in a first orientation with respect to the body in which the interior cavity is unable to accommodate the pen needle connected to the body; and
in a second orientation with respect to the body that is axially further from a second end of the body than the first orientation, to accommodate the pen needle connected to the body within the interior cavity, the second end of the body being opposite to the first end.

11. The self-injection device according to claim 10, wherein the first and second orientations are radial orientations with respect to the body.

12. A self-injection device, comprising:
a pen needle;
a body connectable to the pen needle at a first end of the body; and
a cap having an interior cavity, the cap being connectable to the body in a first orientation with respect to the body in which the interior cavity is unable to accommodate the pen needle connected to the body, and in a second orientation with respect to the body that is axially further from a second end of the body than the first orientation, to accommodate the pen needle connected to the body within the interior cavity, the second end of the body being opposite to the first end;
wherein:
the body comprises a body axial protrusion and a body axial recess, and the cap comprises a cap axial protrusion and a cap axial recess;
in the first orientation, the body axial protrusion axially abuts the cap axial recess and the cap axial protrusion axially abuts the body axial recess; and
in the second orientation, the body axial protrusion axially abuts the cap axial protrusion.

13. The self-injection device according to claim 12, wherein:
the body comprises a first body connector disposed within the pen body axial recess;
the cap comprises a cap connector disposed on an interior of the cap axial protrusion axially adjacent to an end of the cap axial protrusion to interact with the first body connector to secure the cap to the body in the first orientation; and
the first body connector comprises one of a radial protrusion and a radial recess, and the cap connector comprises a remaining one of the radial protrusion and the radial recess.

14. The self-injection device according to claim 13, wherein:
the body further comprises a second body connector disposed axially adjacent to an end of the pen body axial protrusion; and the second body connector comprises one of a second radial protrusion and a second radial recess, to interact with the cap connector to secure the cap to the body in the second orientation.

15. The self-injection device according to claim 13, wherein:
the body further comprises a cartridge container for holding a medicament cartridge in the body, the cartridge container having an axial slot therethrough for viewing a content of the medicament cartridge; and
the cap further comprises a radial protrusion that engages the cartridge container axial slot to secure the cap to the body in the second orientation.

16. The self-injection device according to claim 12, further comprising an anti-rotation feature for preventing rotation of the cap with respect to the body subsequent to connection of the cap to the body.

17. The self-injection device according to claim 16, wherein the anti-rotation feature comprises:
a pair of axially protruding horns disposed on radial sides of the body axial protrusion; and
a pair of axial horn recesses disposed on radial sides of the cap axial recess, the horn recesses corresponding to the horns;
wherein the horns interact with horn recesses when the cap is secured to the body in the first orientation to prevent relative rotation of the cap with respect to the body; and
wherein the horns interact with radial sides of the cap axial protrusion when the cap is secured to the body in the second orientation to prevent relative rotation of the cap with respect to the body.

18. The self-injection device according to claim 16, wherein the anti-rotation feature comprises:
a pair of axially protruding horns disposed on radial sides of the cap axial protrusion; and
a pair of axial horn recesses disposed on radial sides of the body axial recess, the horn recesses corresponding to the horns;
wherein the horns interact with horn recesses when the cap is secured to the body in the first orientation to prevent relative rotation of the cap with respect to the body; and
wherein the horns interact with radial sides of the body axial protrusion when the cap is secured to the body in the second orientation to prevent relative rotation of the cap with respect to the body.

19. A method of using a self-injection device comprising a pen needle, a body, and a cap, the method comprising the operations of:
at a first time, connecting the cap directly to a first end of the body in a first orientation in which a length or volume of the self-injection device is insufficient to house the pen needle connected to the body; and
at a second time, connecting the cap directly to the first end of the body in a second orientation that provides sufficient length or volume in an interior of the cap to house the pen needle connected to the body.

20. A method of using a self-injection device comprising a pen needle, a body, and a cap, the method comprising the operations of:
at a first time, connecting the cap to the body in a first orientation in which a length or volume of the self-injection device is insufficient to house the pen needle connected to the body; and
at a second time, connecting the cap to the body in a second orientation that provides sufficient length or volume in an interior of the cap to house the pen needle connected to the body;
wherein connecting the cap to the body in the first orientation comprises orienting an axial protrusion and an axial recess of the cap to respectively axially abut an axial recess and an axial protrusion of the body; and
wherein connecting the cap to the body in the second orientation comprises orienting the axial cap protrusion to axially abut the axial body protrusion.

21. A self-injection device, comprising:
a pen needle;
a pen body connectable to the pen needle; and
a cap connectable directly to a first end of the pen body:
in a first orientation with respect to the pen body to provide insufficient length or volume in an interior of the cap to house the pen needle connected to the pen body; and
in a second orientation to provide sufficient length or volume in the interior of the cap to house the pen needle connected to the pen body.

* * * * *